United States Patent
Heckroth et al.

(10) Patent No.: US 7,754,782 B2
(45) Date of Patent: Jul. 13, 2010

(54) MEDICAL ADHESIVES FOR SURGERY

(75) Inventors: Heike Heckroth, Odenthal (DE);
Burkhard Köhler, Zierenberg (DE);
Sebastian Dörr, Düsseldorf (DE)

(73) Assignee: Bayer Material Science AG, Leverkusen (DE)

( * ) Notice: Subject to any disclaimer, the term of this patent is extended or adjusted under 35 U.S.C. 154(b) by 5 days.

(21) Appl. No.: 12/164,278

(22) Filed: Jun. 30, 2008

(65) Prior Publication Data
US 2009/0012206 A1  Jan. 8, 2009

(30) Foreign Application Priority Data
Jul. 3, 2007 (EP) .................. 07012984
Nov. 9, 2007 (EP) .................. 07021764

(51) Int. Cl.
*A61L 24/04* (2006.01)
*A61K 31/74* (2006.01)
*A61K 31/785* (2006.01)
*A61F 2/00* (2006.01)
*B05D 3/02* (2006.01)

(52) U.S. Cl. .................. 523/111; 528/58; 528/60; 528/61; 528/68; 424/423; 424/78.27

(58) Field of Classification Search ................ 523/105, 523/111
See application file for complete search history.

(56) References Cited

U.S. PATENT DOCUMENTS

| 4,355,188 A * | 10/1982 | Herold et al. ............. 568/620 |
| 4,806,614 A | 2/1989 | Matsuda et al. |
| 5,156,613 A | 10/1992 | Sawyer |
| 5,173,301 A | 12/1992 | Itoh et al. |
| 5,236,741 A * | 8/1993 | Zwiener et al. .......... 427/385.5 |
| 5,243,012 A * | 9/1993 | Wicks et al. ................. 528/58 |
| 5,506,327 A * | 4/1996 | Yonek et al. ................. 528/45 |
| 5,591,807 A * | 1/1997 | Cai et al. ................... 525/381 |
| 5,807,924 A * | 9/1998 | Becker et al. ............... 524/786 |
| 6,123,667 A | 9/2000 | Poff et al. |
| 6,265,016 B1 | 7/2001 | Hostettler et al. |
| 6,724,292 B2 | 4/2004 | Miyashita et al. |
| 6,897,281 B2 * | 5/2005 | Lubnin et al. ................. 528/44 |
| 7,026,429 B2 * | 4/2006 | Gertzmann et al. .......... 528/45 |
| 7,049,367 B2 * | 5/2006 | Mazanek et al. ............ 524/591 |
| 2003/0135238 A1 | 7/2003 | Milbocker |
| 2004/0048070 A1 * | 3/2004 | Kendall et al. ............ 428/411.1 |
| 2004/0067315 A1 * | 4/2004 | Niesten et al. ............ 427/372.2 |
| 2005/0129733 A1 | 6/2005 | Milbocker et al. |
| 2009/0148683 A1 * | 6/2009 | Ilfrey ......................... 428/215 |
| 2009/0191145 A1 * | 7/2009 | Heckroth et al. ......... 424/78.06 |
| 2009/0221071 A1 * | 9/2009 | Heckroth et al. ............ 435/375 |

FOREIGN PATENT DOCUMENTS

| DE | 69311633 T2 | 10/1997 |
| DE | 10246708 A1 | 4/2004 |
| EP | 0482467 A2 | 4/1992 |
| EP | 1081171 A2 | 3/2001 |
| EP | 1277876 A2 | 1/2003 |
| WO | WO-03/009323 A1 | 1/2003 |

* cited by examiner

*Primary Examiner*—Marc S Zimmer
*Assistant Examiner*—Noah Frank
(74) *Attorney, Agent, or Firm*—Connolly Bove Lodge & Hutz LLP

(57) ABSTRACT

The present invention relates to novel, rapidly curing adhesives based on hydrophilic polyisocyanate prepolymers for use in surgery.

11 Claims, No Drawings

MEDICAL ADHESIVES FOR SURGERY

RELATED APPLICATIONS

This application claims benefit to European Patent Application No. 07 012 984.6, filed Jul. 3, 2007 and European Patent Application No. 07 021 764.1, filed Nov. 19, 2007, which is incorporated herein by reference in its entirety for all useful purposes.

BACKGROUND OF THE INVENTION

The present invention relates to novel, rapidly curing adhesives based on hydrophilic polyisocyanate prepolymers for use in surgery.

In recent years, increasing interest has developed in the replacement or complementation of surgical sutures through the use of suitable adhesives. Particularly in the field of plastic surgery, in which particular value is placed on thin, as far as possible invisible scars, adhesives are being increasingly used.

Tissue adhesives must have a number of properties in order to be accepted among surgeons as a substitute for sutures. These include ease of use and an initial viscosity such that the adhesive cannot penetrate into deeper tissue layers or run off. In classical surgery, rapid curing is required, whereas in plastic surgery correction of the adhesive suture should be possible and thus the curing rate should not be too rapid (ca. 5 mins). The adhesive layer should be a flexible, transparent film, which is not degraded in a time period of less than three weeks. The adhesive must be biocompatible and must not display histotoxicity, nor thrombogenicity or potential allergenicity.

Various materials which are used as tissue adhesives are commercially available. These include the cyanoacrylates Dermabond® (octyl 2-cyanoacrylate) and Histoacryl Blue® (butyl cyanoacrylate). However, the rapid curing time and the brittleness of the adhesion site limit their use. Owing to their poor biodegradability, cyanoacrylates are only suitable for external surgical sutures.

As alternatives to the cyanoacrylates, biological adhesives such as peptide-based substances (BioGlue®) or fibrin adhesives (Tissucol) are available. Apart from their high cost, fibrin adhesives are characterized by relatively weak adhesive strength and rapid degradation, so that this is only usable for smaller incisions in untensioned skin.

Isocyanates-containing adhesives are all based on an aromatic diisocyanate and a hydrophilic polyol, the isocyanates TDI and MDI preferably being used (US 20030135238, US 20050129733). Both can bear electron-withdrawing substituents in order to increase their reactivity (WO-A 03/9323).

Difficulties until now were the low mechanical strength (U.S. Pat. No. 5,156,613), excessively slow curing rate (U.S. Pat. No. 4,806,614), excessively rapid biodegradability (U.S. Pat. No. 6,123,667) and uncontrolled swelling (U.S. Pat. No. 6,265,016).

According to US patent 20030135238, only polyurethane prepolymers with a trifunctional or branched structure which are also capable of forming hydrogels are suitable adhesives. The adhesive must also be capable of forming a covalent bond to the tissue. US 20030135238 and US 20050129733 describe the synthesis of trifunctional, ethylene oxide-rich TDI- and IPDI-(US 20030135238) based prepolymers which react with water or with tissue fluids to give the hydrogel. Sufficiently rapid curing was until now only attained with the use of aromatic isocyanates, which however react with the formation of foam. This results in penetration of the adhesive into the wound and hence in the wound edges being pushed part, which results in poorer healing with increased scarring. In addition, the mechanical strength and the adhesion of the adhesive layer is decreased by the foam formation. In addition, on account of the higher reactivity of the prepolymers, reaction of the isocyanate radicals with the tissue takes place, as a result of which denaturation, recognizable through white coloration of the tissue, often occurs.

As a replacement for the aromatic isocyanates, lysine diisocyanate has been studied, but owing to its low reactivity this reacts only slowly or not at all with tissue (US 20030135238).

In order to increase their reactivity, aliphatic isocyanates have been fluorinated (U.S. Pat. No. 5,173,301), however this resulted in spontaneous autopolymerization of the isocyanate.

EP-A 0 482 467 describes the synthesis of a surgical adhesive based on an aliphatic isocyanate (preferably HDI) and a polyethylene glycol (Carbowax 400). Curing takes place on addition of 80-100% water and a metal carboxylate (potassium octanoate) as catalyst, during which a foam is formed, which is stabilized with silicone oil.

Systems based on aliphatic isocyanates display only insufficient reactivity and hence an excessively slow curing time. Although the reaction rate could be increased by the use of metal catalysts, as described in EP-A 0 482 467, this resulted in the formation of a foam, with the problems described above.

The fundamental suitability of aspartate esters for the crosslinking of prepolymers is well known in the state of the art in the context of surface coatings and is for example described in EP-A 1 081 171 or DE-A 102 46 708.

EMBODIMENTS OF THE INVENTION

An embodiment of the present invention is an adhesive system comprising A) prepolymers comprising isocyanate groups obtained from A1) aliphatic isocyanates; and A2) polyols with number-averaged molecular weights of $\geq 400$ g/mol and average OH group contents of from 2 to 6; and B) amino group-containing aspartate esters of general formula (I)

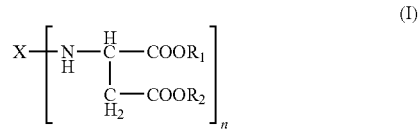

wherein X is an n-valent organic radical obtained by removal of the primary amino groups of an n-functional amine; $R_1$ and $R_2$ are, identically or differently, organic radicals comprising no Zerevitinov active hydrogen; and n is a whole number of at least 2; and/or C) reaction products of prepolymers comprising isocyanate groups with aspartate esters according to B).

Another embodiment of the present invention is the above adhesive system, wherein said aliphatic isocyanates in A1) have only aliphatically or cycloaliphatically bound isocyanate groups.

Another embodiment of the present invention is the above adhesive system, wherein said aliphatic isocyanates in A1) have an average NCO group content of from 2 to 2.4.

Another embodiment of the present invention is the above adhesive system, wherein said polyols in A2) have number-averaged molecular weights of 4000 to 8500 g/mol.

Another embodiment of the present invention is the above adhesive system, wherein said polyols in A2) have average OH group contents of from 3 to 4.

Another embodiment of the present invention is the above adhesive system, wherein A2) comprises polyalkylene oxide polyethers.

Another embodiment of the present invention is the above adhesive system, wherein A2) comprises polyalkylene oxide polyethers and said polyalkylene oxide polyethers have a content of ethylene oxide-based units of 60 to 90% based on the total quantity of alkylene oxide units contained.

Another embodiment of the present invention is the above adhesive system, wherein X is derived from 4-diaminobutane, 1,6-diaminohexane or 2,2,4- or 2,4,4-trimethyl-1,6-diaminohexane as n-functional amines, $R_1$ and $R_2$ are, independently of one another, a $C_1$ to $C_{10}$ alkyl radical, and n=2.

Another embodiment of the present invention is the above adhesive system, wherein said two-component adhesive system does not comprise B).

Another embodiment of the present invention is the above adhesive system, wherein said reaction products of C) are obtained by reaction of said prepolymers with said aspartate esters in a ratio of isocyanate-reactive groups to isocyanate groups of between 15 to 1 and 4 to 1.

Yet another embodiment of the present invention is a tissue adhesive for human or animal tissue comprising the above adhesive system.

Yet another embodiment of the present invention is a process for the closure or binding of cellular tissues, comprising applying at least one of the above adhesive systems to the cellular tissue to be closed or bound.

Another embodiment of the present invention is the above process, wherein said cellular tissue is human or animal tissue.

Yet another embodiment of the present invention is an agent for the closure or binding of cellular tissues comprising the above adhesive system.

Yet another embodiment of the present invention is an adhesive film and/or laminated part comprising the above adhesive system.

Yet another embodiment of the present invention is a two-chamber dispensing system comprising the above adhesive system.

DESCRIPTION OF THE INVENTION

The objective on which the present invention is based was thus to produce a tissue adhesive which:
  forms a strong bond to the tissue
  forms a transparent film
  forms a flexible suture
  owing to regulated viscosity is easy to apply and cannot penetrate into deeper tissue layers
  depending on the field of use has a curing time from a few seconds up to 10 minutes
  displays no significant exothermicity on curing
  is biocompatible, and which, like its degradation products, displays no cell or tissue toxicity In the context of the present invention, tissues are understood to mean associations of cells which consist of cells of the same form and function such as surface tissue (skin), epithelial tissue, myocardial, connective or stromal tissue, muscles, nerves and cartilage. These also include inter alia all organs made up of associations of cells such as the liver, kidneys, lungs, heart, etc.

Surprisingly it has now been found that this problem could be solved by a combination of isocyanate group-containing prepolymers based on aliphatic isocyanates with amino group-containing aspartate esters.

The subject matter of the present invention are therefore adhesive systems comprising
A) isocyanate group-containing prepolymers obtainable from
  A1) aliphatic isocyanates and
  A2) polyols with number-averaged molecular weights of $\geq 400$ g/mol and average OH group contents of from 2 to 6 and
B1) amino group-containing aspartate esters of the general formula (I)

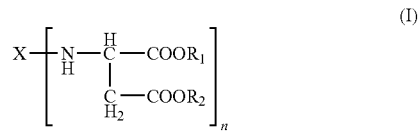

wherein
  X is an n-valent organic radical, which is obtained by removal of the primary amino groups of an n-functional amine,
  $R_1$, $R_2$ are the same or different organic radicals, which contain no Zerevitinov active hydrogen and
  n is a whole number of at least 2 and/or
C) reaction products of isocyanate group-containing prepolymers with aspailate esters according to component B).

For the definition of Zerevitinov active hydrogen, reference is made to Römpp Chemie Lexikon, Georg Thieme Verlag Stuttgart. Preferably, groups with Zerevitinov active hydrogen are understood to mean OH, NH or SH.

The adhesive systems according to the invention are consisting of at least 2 components. Preferably they comprise a component containing the compounds of A) and a second component containing the compounds of B) and/or C).

The isocyanate group-containing prepolymers used in A) are obtainable by reaction of isocyanates with hydroxy group-containing polyols optionally with the addition of catalysts, auxiliary agents and additives.

As isocyanates in A1), for example monomeric aliphatic or cycloaliphatic di- or triisocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis-(4,4'-isocyanatocyclohexyl)methanes or mixtures thereof of any isomer content, 1,4-cyclo-hexylene diisocyanate, 4-isocyanatomethyl-1,8-octane diisocyanate (nonane triisocyanate), and alkyl 2,6-diisocyanatohexanoates (lysine diisocyanate) with C1-C8 alkyl groups can be used.

In addition to the aforesaid monomeric isocyanates, higher molecular weight derivatives thereof of uretdione, isocyanurate, urethane, allophanate, biuret, iminooxadiazinedione or oxadiazinetrione structure and mixtures thereof can also be used.

Preferably, isocyanates of the aforesaid nature with exclusively aliphatically or cycloaliphatically bound isocyanate groups or mixtures thereof are used in A1).

The isocyanates or isocyanate mixtures used in A1, preferably have an average NCO group content of from 2 to 4, particularly preferably 2 to 2.6 and quite particularly preferably 2 to 2.4.

In a particularly preferable embodiment, hexamethylene diisocyanate is used in A1).

For synthesis of the prepolymer, essentially all polyhydroxy compounds with 2 or more OH groups per molecule known per se to a person skilled in the art can be used in A2). These can for example be polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols, polyester polycarbonate polyols or any mixtures thereof one with another.

The polyols used in A2) preferably have an average OH group content of from 3 to 4.

Furthermore, the polyols used in A2) preferably have a number-averaged molecular weight of 400 to 20 000 g/mol, particularly preferably 2000 to 10 000 g/mol and quite particularly preferably 4000 to 8500.

Polyether polyols are preferably polyalkylene oxide polyethers based on ethylene oxide and optionally propylene oxide.

These polyether polyols are preferably based on starter molecules with two or more functional groups such as alcohols or amines with two or more functional groups.

Examples of such starters are water (regarded as a diol), ethylene glycol, propylene glycol, butylene glycol, glycerine, TMP, sorbitol, pentaerythritol, triethanolamine, ammonia or ethylenediamine.

Preferred polyalkylene oxide polyethers correspond to those of the aforesaid nature and have a content of ethylene oxide-based units of 50 to 100%, preferably 60 to 90%, based on the overall quantities of alkylene oxide units contained.

Preferred polyester polyols are the polycondensation products, known per se, of di- and optionally tri- and tetraols and di- and optionally tri- and tetracarboxylic acids or hydroxycarboxylic acids or lactones. Instead of the free polycarboxylic acids, the corresponding polycarboxylic acid anhydrides or corresponding polycarboxylate esters of lower alcohols can also be used for the production of the polyesters.

Examples of suitable diols are ethylene glycol, butylene glycol, diethylene glycol, triethylene glycol, polyalkylene glycols such as polyethylene glycol and also 1,2-propanediol, 1,3-propane-diol, 1,3-butanediol, 1,4-butanediol, 1,6-hexanediol and isomers, neopentyl glycol or neopentyl glycol hydroxypivalate, with 1,6-hexanediol and isomers, 1,4-butanediol, neopentyl glycol and neopentyl glycol hydroxypivalate being preferred. As well as these, polyols such as trimethylol-propane, glycerine, erythritol, pentaerythritol, trimethylolbenzene or trishydroxyethyl isocyanurate can also be used.

As dicarboxylic acids, phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid can be used. The corresponding anhydrides can also be used as the source of acid.

Provided that the average functional group content of the polyol to be esterified is >2, monocarboxylic acids, such as benzoic acid and hexanecarboxylic acid can also be used as well.

Preferred acids are aliphatic or aromatic acids of the aforesaid nature. Particularly preferred are adipic acid, isophthalic acid and phthalic acid.

Examples of hydroxycarboxylic acids, which can also be used as reaction partners in the production of a polyester polyol with terminal hydroxy groups are hydroxycaproic acid, hydroxybutyric acid, hydroxydecanoic acid, hydroxystearic acid and the like. Suitable lactones are caprolactone, butyrolactone and homologues. Caprolactone is preferred.

Likewise, polycarbonates having hydroxy groups, preferably polycarbonate diols, with number-averaged molecular weights $M_n$ of 400 to 8000 g/mol, preferably 600 to 3000 g/mol, can be used. These are obtainable by reaction of carboxylic acid derivatives, such as diphenyl carbonate, dimethyl carbonate or phosgene, with polyols, preferably diols.

Possible examples of such diols are ethylene glycol, 1,2- and 1,3-propanediol, 1,3- and 1,4-butane-diol, 1,6-hexanediol, 1,8-octanediol, neopentyl glycol, 1,4-bishydroxymethylcyclohexane, 2-methyl-1,3-propanediol, 2,2,4-trimethylpentane-1,3-diol, dipropylene glycol, polypropylene glycols, dibutylene glycol, polybutylene glycols, bisphenlol A and lactone-modified diols of the aforesaid nature.

Polyether polyols of the aforesaid nature are preferably used for the synthesis of the prepolymer.

For the production of the prepolymer, the compounds of the component A1) are reacted with those of the component A2) preferably with an NCO/OH ratio of 4:1 to 12:1, particularly preferably 8:1, and then the content of unreacted compounds of the component A) is separated by suitable methods. Thin film distillation is normally used for this, whereby low residual monomer products with residual monomer contents of less than 1 wt. %, preferably less than 0.5 wt. %, quite particularly preferably less than 0.1 wt. %, are obtained.

If necessary, stabilizers such as benzoyl chloride, isophthaloyl chloride, dibutyl phosphate, 3-chloropropionic acid or methyl tosylate can be added during the production process.

The reaction temperature here is 20 to 120° C., preferably 60 to 100° C.

The production of the amino group-containing polyaspartate ester B) is effected in a known manner by reaction of the corresponding primary at least bifunctional amine $X(NH_2)_n$ with maleate or fumarate esters of the general formula

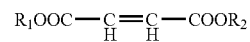

Preferred maleate or fumarate esters are dimethyl maleate, diethyl maleate, dibutyl maleate and the corresponding fumarate esters.

Preferred primary at least bifunctional amines $X(NH_2)_n$ are ethylenediamine, 1,2-diaminopropane, 1,5-diaminopentane, 2-methyl-1,5-diaminopentane, 1,4-diaminobutane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethyl-cyclohexane, 2,4- and/or 2,6-hexahydrotoluoylenediamine, 2,44- and/or 4,4'-diaminodicyclohexylmethane, 3,3'-dimethyl-4,4'-diaminodicyclohexyl-methane, 2,4,4'-triamino-5-methyldicyclohexylmethane and polyether amines with aliphatically bound primary amino groups with a number-averaged molecular weight $M_n$ of 148 to 6000 g/mol.

Particularly preferred primary at least bifunctional amines are 1,5-diaminopentane, 2-methyl-1,5-diaminopentane, 4-diaminobutane, 1,6-diamino-hexane and 2,2,4- and/or 2,4,4-trimethyl-1,6-diaminohexane.

Preferably, $R_1$ and $R_2$ independently of one another are $C_1$ to $C_{10}$ alkyl radicals, particularly preferably methyl or ethyl radicals.

In a preferred embodiment of the invention, $R_1=R_2=$ethyl, X being based on or added to 2-methyl-1,5-diaminopentane as the n-functional amine.

Preferably, n in formula (I) for the description of the functionality of the n-functional amine is a whole number from 2 to 6, particularly preferably 2 to 4.

The production of the amino group-containing aspartate ester B) from the said starting materials is effected according to DE-A 69 311 633, preferably within the temperature range from 0 to 100° C., the starting materials being used in quantity proportions such that for every primary amino group at least one, preferably exactly one, olefinic double bond is removed, wherein starting materials possibly used in excess can be removed by distillation after the reaction. The reaction can be effected neat or in the presence of suitable solvents such as methanol, ethanol, propanol or dioxan or mixtures of such solvents.

In order to reduce the equivalent weight of amino groups, instead of or in addition to the aspartate esters used in B), it is also possible to produce the amino group-containing reaction products of isocyanate group-containing prepolymers with the aspartate esters in a separate prereaction of the two components and then to use these reaction products as a higher molecular weight amino group-containing curing component C).

Preferably, ratios of isocyanate-reactive groups to isocyanate groups of between 50 to 1 and 1.5 to 1, particularly preferably between 15 to 1 and 4 to 1, are used for this.

Here, the isocyanate group-containing prepolymer to be used for this can correspond to that of the component A) or else be constituted differently from the components listed as possible components of the isocyanate group-containing prepolymers in the context of this application.

The advantage of this modification by pre-extension of the component B) is that the equivalent weight and equivalent volume of the amine curing agent component is modifiable within a clear range. As a result, commercially available 2-chamber dispensing systems can be used for application, in order to obtain an adhesive system which with current chamber volume ratios can be adjusted to the desired ratio of amino groups to NCO groups.

The adhesive systems according to the invention are obtained by mixing of the prepolymer with the amino group-containing aspartate esters of the components B) and/or C). The ratio of amino groups to free NCO groups is preferably 1:1.5 to 1:1, particularly preferably 1:1.

Directly after mixing together of the individual components, the 2-component adhesive systems according to the invention preferably have a shear viscosity at 23° C. of 1000 to 10 000 mPas, particularly preferably 2000 to 8000 mPas and quite particularly preferably 2500 to 5000 mPas.

At 23° C., the rate until complete crosslinking and curing of the adhesive is attained is typically 30 secs to 10 mins, preferably 1 min to 8 min, particularly preferably 1 min to 5 mins.

A further subject of the invention is the adhesive films obtainable from the adhesive systems according to the invention and laminated parts produced therefrom.

In a preferred embodiment, the adhesive systems according to the invention are used as tissue adhesives for the closure of wounds in associations of human or animal cells, so that clamping or suturing for closure can to a very large extent be dispensed with.

The tissue adhesives according to the invention can be used both in vivo and also in vitro, with use in vivo, for example for wound treatment after accidents or operations, being preferred.

Hence a process for the closure or binding of cellular tissues, characterized in that the adhesive systems according to the invention are used, is also an object of the present invention.

Likewise a subject of the invention is the use of such adhesive systems for the production of an agent for the closure or binding of cellular tissues and the 2-chamber dispensing systems containing the components of the adhesive system fundamental to the invention which are necessary for its application.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Unless otherwise stated, all percentages quoted are based on weight.

As a tissue substitute, beef was used. In each case, two pieces of meat (l=4 cm, h=0.3 cm, b=1 cm) were painted at the ends over a 1 cm width with the adhesive and glued overlapping. The stability of the adhesive layer was in each case tested by pulling.

Desmophen® DE 550 U: trimethylolpropane-started propylene glycol

DE 1470 EV: N,N,N',N'-tetrakis(2-hydroxypropyl)ethylenediamine

Example 1

Prepolymer A-1

465 g of HDI and 2.35 g of benzoyl chloride were placed in a 1 l four-necked flask. 931.8 g of a polyether with an ethylene oxide content of 63% and a propylene oxide content of 37% (each based on the total alkylene oxide content) started with TMP (3-functional) were added within 2 hrs at 80° C. and then stirred for a further hour. Next, the excess HDI was distilled off by thin film distillation at 130° C. and 0.1 mm Hg. 980 g (71%) of the prepolymer with an NCO content of 2.53% were obtained. The residual monomer content was <0.03% HDI.

Example 2

Prepolymer A-2

119 g of Desmodur I (IPDI) and 0.52 g of benzoyl chloride were placed in a 1 l four-necked flask. 180.3 g of a polyether with an ethylene oxide content of 63% and a propylene oxide content of 37% (each based on the total alkylene oxide content) started with glycerine (3-functional) were added within 2 hrs at 80° C. and then stirred for a further hour. Next, the excess IPDI was distilled off by thin film distillation at 130°

C. and 0.1 mm Hg. 130 g (81%) of the prepolymer with an NCO content of 2.56% were obtained. The residual monomer content was <0.03% HDI.

Example 3

Aspartate B 1 mol of 2-methyl-1,5-pentandiamine was slowly added dropwise to 2 mols of diethyl maleate under a nitrogen atmosphere, so that the reaction temperature did not exceed 60° C. The mixture was then heated at 60° C. until diethyl maleate was no longer detectable in the reaction mixture.

Example 3a

Aspartate Component Partially Pre-Extended with Isocyanate Group-Containing Prepolymer 1000 g of HDI (hexamethylene diisocyanate), 1 g of benzoyl chloride and 1 g of methyl para-toluenesulphonate were placed with stirring in a 4 l four-necked flask. 1000 g of a bifunctional polypropylene glycol polyether with an average molecular weight of 2000 g/mol were added within 3 hours at 80° C. and then stirred for a further hour. The excess HDI was then distilled off by thin film distillation at 130° C. and 0.1 mm Hg. The prepolymer obtained has an NCO content of 3.7%.

200 g of the prepolymer were fed with stirring at room temperature into 291 g of the aspartate B) from 2,4,4-trimethyl-1,6-diaminohexane in a 1 l four-necked flask. This was stirred for a further two hours, until isocyanate groups were no longer detectable by IR spectroscopy. The product obtained had a viscosity of 3740 mPas and an NH equivalent weight of 460 g/eq.

Example 3b

Aspartate Component Partially Pre-Extended with Isocyanate Group-Containing Prepolymer 1000 g of HDI (hexamethylene diisocyanate), 1 g of benzoyl chloride and 1 g of methyl para-toluenesulphonate were placed with stirring in a 4 l four-necked flask. 1000 g of a bifunctional polypropylene glycol polyether with an average molecular weight of 8000 g/mol were added within 3 hours at 80° C. and stirred for a further hour. The excess HDI was then distilled off by thin film distillation at 130° C. and 0.1 mm Hg. The prepolymer obtained has an NCO content of 1.66%.

200 g of the prepolymer were fed with stirring at room temperature into 244 g of the aspartate B) from 2-methyl-1, 5-pentandiamine in a 1 l l four-necked flask. This was stirred for a further two hours, until isocyanate groups were no longer detectable by IR spectroscopy. The product obtained had a viscosity of 3940 mPas and an NH equivalent weight of 460 g/eq.

Example 3c

Aspartate Component Partially Pre-Extended with Isocyanate Group-Containing Prepolymer A-1

200 g of the prepolymer from A-1 were fed with stirring at room temperature into 200 g of the aspartate B) from 2-methyl-1,5-pentandiamine in a 1 l four-necked flask. This was stirred for a further two hours, until isocyanate groups were no longer detectable by IR spectroscopy. The product obtained had a viscosity of 11700 mPas and an NH equivalent weight of 543 g/eq.

Example 4

Tissue Adhesive 10 g of the prepolymer A-1 were stirred well in a beaker with equivalent quantities of the amino group-containing aspartate ester (aspartate B). Directly after this, the reaction mixture was applied thinly onto the tissue to be glued.

| Amine used based on aspartate B | Processing time | Curing time (adhesion to meat) |
|---|---|---|
| 2-methyl-1,5-diaminopentane | 5 mins | 1 min |
| 2,4,4-trimethyl-1,6-diaminohexane | 10 mins | 1 min |
| 4,7,10-trioxa-1,13-tridecanediamine | 6 mins | 1-5 mins |
| 3,3'-diamino-N-methyldipropylamine | 15 secs | Processing time too rapid for application |
| 1,4-bis-(3-aminopropyloxy)-butane | 6 mins | 1-5 mins |
| 1,3-diamino-2,2-dimethylpropane | >1 hr | / |
| 1,3-bis-(aminomethyl)-cyclohexane | 8 mins | 1-5 mins |
| 1,7-diaminoheptane | 4 mins | 1-5 mins |
| 1,3-diaminopropane | 3 mins | 1-5 mins |
| Isophoronediamine (IPDA) | >1 hr | / |
| 3a | 6 mins | 1-5 mins |
| 3b | 6 mins | 1-5 mins |
| 3c | 7 mins | 1.5 mins |

Example 5

Tissue Adhesive 10 g of the prepolymer A-2 were stirred well in a beaker with equivalent quantities of the amino group-containing aspartate ester (aspartate B). Directly after this, the reaction mixture was thinly applied onto the tissue to be glued. Curing to a transparent film with associated strong adhesion had taken place within 5 mins.

Reference Examples

1. On application of the prepolymer A to tissue, no curing and hence no adhesion occurred.

2. On application to meat according to EP 0482467, a mixture of 10 g of prepolymer A with 1% (0.1 g) sodium octanoate and different quantities (10 to 200%) of water resulted in foam formation on the tissue. No adhesion was observed.

3. A mixture of 10 g of prepolymer A with equivalent quantities of triethanolamine or DE 1470 EV such as is commonly used for curing, likewise resulted in no adhesion on application to meat.

4. A mixture of 10 g of prepolymer A with equivalent quantities of Desmophen DE 550 U as a polyol typically used for crosslinking occasionally resulted in curing on the tissue, but not in adhesion.

5. Prepolymer A was prepared as described in Example 1 with IPDI instead of HDI. The prepolymer obtained was mixed according to US 20030 135 238 with quantities of water from 10%-200% based on the prepolymer and applied onto the tissue. No adhesion was observed.

6. Prepolymer A was prepared as described in Example 1 with TDI instead of DTI. The prepolymer obtained was treated according to US 20030135238 and US 20050129733 with different quantities of water and applied onto meat. Strong adhesion with foam formation took place.

The invention claimed is:

1. A process for the closure or binding of cellular tissues, comprising applying at least one adhesive system comprising
   A) prepolymers comprising isocyanate groups obtained from
      A1) aliphatic isocyanates; and
      A2) polyols with number-averaged molecular weights of $\geq 400$ g/mol and average OH group contents of from 2 to 6;
   and
   B) amino group-containing aspartate esters of general formula (I)

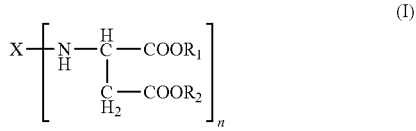

(I)

wherein
   X is an n-valent organic radical obtained by removal of the primary amino groups of an n-functional amine;
   $R_1$ and $R_2$
      are, identically or differently, organic radicals comprising no Zerevitinov active hydrogen; and
   n is a whole number of at least 2;
   and/or
   C) reaction products of prepolymers comprising isocyanate groups with aspartate
      esters according to B)
   to the cellular tissue to be closed or bound.

2. The process of claim 1, wherein said aliphatic isocyanates in A1) have only aliphatically or cycloaliphatically bound isocyanate groups.

3. The process of claim 1, wherein said aliphatic isocyanates in A1) have an average NCO group content of from 2 to 2.4.

4. The process of claim 1, wherein said polyols in A2) have number-averaged molecular weights of from 4000 to 8500 g/mol.

5. The process of claim 1, wherein said polyols in A2) have average OH group contents of from 3 to 4.

6. The process of claim 1, wherein A2) comprises polyalkylene oxide polyethers.

7. The process of claim 6, wherein said polyalkylene oxide polyethers have a content of ethylene oxide-based units of from 60 to 90% based on the total quantity of alkylene oxide units contained in said polyalkylene oxide polyethers.

8. The process of claim 1, wherein X is derived from 4-diaminobutane, 1,6-diaminohexane, 1,5-diaminopentane, or 2-methyl-1,5-diaminopentane as n-functional amines; $R_1$ and $R_2$ are, independently of one another, a $C_1$ to $C_{10}$ alkyl radical; and n is 2.

9. The process of claim 1, wherein said two-component adhesive system does not comprise B).

10. The process of claim 1, wherein said reaction products of C) are obtained by reaction of said prepolymers with said aspartate esters in a ratio of isocyanate-reactive groups to isocyanate groups of between 15 to 1 and 4 to 1.

11. The process of claim 1, wherein said cellular tissue is human or animal tissue.

* * * * *